(12) United States Patent
Johnson et al.

(10) Patent No.: US 8,019,438 B2
(45) Date of Patent: Sep. 13, 2011

(54) ANCHOR FOR ELECTRODE DELIVERY SYSTEM

(75) Inventors: Eric T. Johnson, Temecula, CA (US); Bruce A. Tockman, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1098 days.

(21) Appl. No.: 11/168,282

(22) Filed: Jun. 28, 2005

(65) Prior Publication Data

US 2006/0293741 A1    Dec. 28, 2006

(51) Int. Cl.
*A61N 1/00* (2006.01)
*A61B 5/00* (2006.01)

(52) U.S. Cl. ........ 607/116; 607/117; 607/118; 607/122; 600/370; 600/371; 600/372; 600/373; 600/374

(58) Field of Classification Search .......... 607/116–118, 607/122; 600/370–374
See application file for complete search history.

(56) References Cited

U.S. PATENT DOCUMENTS

| | | | |
|---|---|---|---|
| 4,559,951 A * | 12/1985 | Dahl et al. ..................... 600/374 |
| 5,009,229 A | 4/1991 | Grandjean et al. |
| 5,170,802 A | 12/1992 | Mehra |
| 5,221,261 A | 6/1993 | Termin et al. |
| 5,224,491 A | 7/1993 | Mehra |
| 5,261,419 A * | 11/1993 | Osypka .......................... 607/122 |
| 5,397,341 A * | 3/1995 | Hirschberg et al. ............ 607/122 |
| 5,449,372 A | 9/1995 | Schmaltz et al. |
| 5,531,779 A | 7/1996 | Dahl et al. |
| 5,566,680 A * | 10/1996 | Urion et al. .................... 600/561 |
| 5,649,906 A | 7/1997 | Gory et al. |
| 5,807,306 A * | 9/1998 | Shapland et al. ............... 604/21 |
| 5,941,869 A * | 8/1999 | Patterson et al. ............. 604/508 |
| 5,951,597 A * | 9/1999 | Westlund et al. ............. 607/126 |
| 5,954,761 A * | 9/1999 | Machek et al. ............... 607/126 |
| 6,136,021 A | 10/2000 | Tockman et al. |
| 6,161,029 A | 12/2000 | Spreigl et al. |
| 6,315,778 B1 * | 11/2001 | Gambale et al. ................ 606/41 |
| 6,319,242 B1 * | 11/2001 | Patterson et al. ............. 604/508 |
| 8,397,109 | 5/2002 | Cammilli et al. |
| 6,438,427 B1 | 8/2002 | Rexhausen et al. |
| 6,682,526 B1 * | 1/2004 | Jones et al. ..................... 606/32 |
| 6,689,056 B1 * | 2/2004 | Kilcoyne et al. .............. 600/300 |
| 6,697,676 B2 | 2/2004 | Dahl et al. |
| 6,961,621 B2 * | 11/2005 | Krishnan et al. ............. 607/126 |
| 6,997,951 B2 * | 2/2006 | Solem et al. ................. 623/2.37 |
| 7,044,967 B1 * | 5/2006 | Solem et al. ................. 623/2.36 |
| 7,184,842 B2 * | 2/2007 | Seifert et al. ................. 607/126 |
| 7,330,765 B2 * | 2/2008 | Haldeman ..................... 607/126 |

(Continued)

FOREIGN PATENT DOCUMENTS

JP        06125991 A  *  5/1994

*Primary Examiner* — Niketa I Patel
*Assistant Examiner* — Nicole F Lavert
(74) *Attorney, Agent, or Firm* — Faegre & Benson LLP (57) ABSTRACT

The present invention is device for delivering an electrode into a lateral vein of the coronary sinus. The device includes a support structure, a stent, a tether coupled to the stent and a removable sheath disposed about the stent. The stent is carried on the support structure and is deployable from a first collapsed configuration to a second expanded configuration for engaging the inner walls of the selected vessel. The sheath is sized to retain the stent in the first collapsed configuration. The electrode is carried on the stent or on a lead threaded over the tether.

20 Claims, 10 Drawing Sheets

U.S. PATENT DOCUMENTS

| | | |
|---|---|---|
| 2002/0026228 A1 | 2/2002 | Schauerte |
| 2002/0138129 A1* | 9/2002 | Armstrong et al. .......... 623/1.11 |
| 2003/0105506 A1* | 6/2003 | Krishnan et al. ............. 607/126 |
| 2003/0199961 A1 | 10/2003 | Bjorklund et al. |
| 2003/0204231 A1 | 10/2003 | Hine et al. |
| 2004/0015193 A1 | 1/2004 | Lamson et al. |
| 2004/0148008 A1* | 7/2004 | Goodson et al. ............. 623/1.12 |
| 2005/0222563 A1* | 10/2005 | McDaniel et al. ............... 606/41 |
| 2005/0251238 A1* | 11/2005 | Wallace et al. ............... 607/126 |
| 2006/0241737 A1* | 10/2006 | Tockman et al. ............. 607/126 |

* cited by examiner

ANCHOR FOR ELECTRODE DELIVERY SYSTEM

FIELD OF THE INVENTION

The present invention relates to a device for delivering cardiac leads into the heart. The present invention further relates to a cardiac lead and a device for delivering a cardiac lead into a distal portion of a branch vessel of the coronary sinus.

BACKGROUND

Cardiac function management systems are used to treat arrhythmias and other abnormal heart conditions. Such systems generally include cardiac leads implanted in the heart for delivering an electrical pulse to the cardiac muscle, for sensing electrical signals produced in the cardiac muscle, or for both delivering and sensing. The lead typically consists of a flexible conductor defining a central channel or lumen surrounded by an insulating sheath extending from an electrode at a distal end to a connector pin at a proximal end.

Cardiac lead placement may be accomplished by introducing the lead through a major blood vessel and advancing the distal end of the lead to a final destination in or near the heart. To facilitate cannulation of the vasculature, it is often helpful to first advance a guide catheter through the desired vascular path. The guide catheter must be sized to accommodate the lead and to provide sufficient support, alone or in combination with a stylet, as the lead is advanced through the vasculature. Such guide catheters are often too awkward or bulky to successfully and efficiently navigate the very small distal lateral branch vessels of the coronary sinus. Another difficulty with implanting leads in this fashion is that the cardiac lead has a tendency to become dislodged during guide catheter removal.

Another difficulty with cardiac lead placement is that a traditional lead may be too bulky for placement into narrower vessels. Even if placement of the lead is possible, the lead may block or impede fluid flow through narrower vessels to an unacceptable degree.

Accordingly, there is a need in the art for a reliable low profile lead and lead implantation system that does not necessarily require the use of a guide catheter. There is a further need for a lead implantation system that may also serve to anchor the lead at the implant site.

BRIEF SUMMARY OF THE INVENTION

According to one embodiment, the present invention is an electrode delivery system for delivering an electrode into a coronary vein. The electrode delivery system includes a support structure having a proximal end and a distal end, a stent, a tether and a removable sheath. The stent is deployable from a first collapsed configuration to a second expanded configuration, is removably coupled about the distal end of the support structure and is sized to receive at least a portion of a lead. The tether is coupled to the stent and has a first portion extending distal to the stent and a second portion extending proximally from the first portion. The removable sheath is disposed around the stent and is sized to retain the stent in the first collapsed configuration. In the second configuration, the stent frictionally engages the coronary vein to anchor the tether. The support structure may be a guide catheter or a cardiac lead. The stent may include an electrode electrically coupled to the tether.

According to another embodiment, the present invention is a device for delivering an electrode into a branch vein of the coronary sinus. The device includes a tether having a distal end and a proximal end and an expandable stent means for fixing an electrode a selected vessel. The tether has a first portion extending distal to the stent means and a second portion extending proximally from the first portion. The device further includes a sheath removable disposed about the stent means and an electrode coupled to the stent means.

According to still another embodiment, the present invention is a method for implanting an electrode into a branch vein of the coronary sinus. A support structure carrying a stent is advanced into the branch vein. The stent is coupled to a tether and is retained in a collapsed configuration about the support structure by a sheath. The sheath is at least partially removed. The stent is deployed at least partially into an expanded configuration in frictional engagement with an inner wall of the branch vein at a fixation location. An electrode coupled to the stent is positioned in contact with a surface of a heart. In one embodiment, the support structure is withdrawn and a cardiac lead having an electrode is threaded over the tether into the branch vein. In another embodiment the support structure is a cardiac lead having an electrode. In another embodiment, the electrode is carried on the stent.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 2A-2E are side views of an electrode delivery system according to one embodiment of the present invention in various stages of deployment.

DETAILED DESCRIPTION

Figure 1:
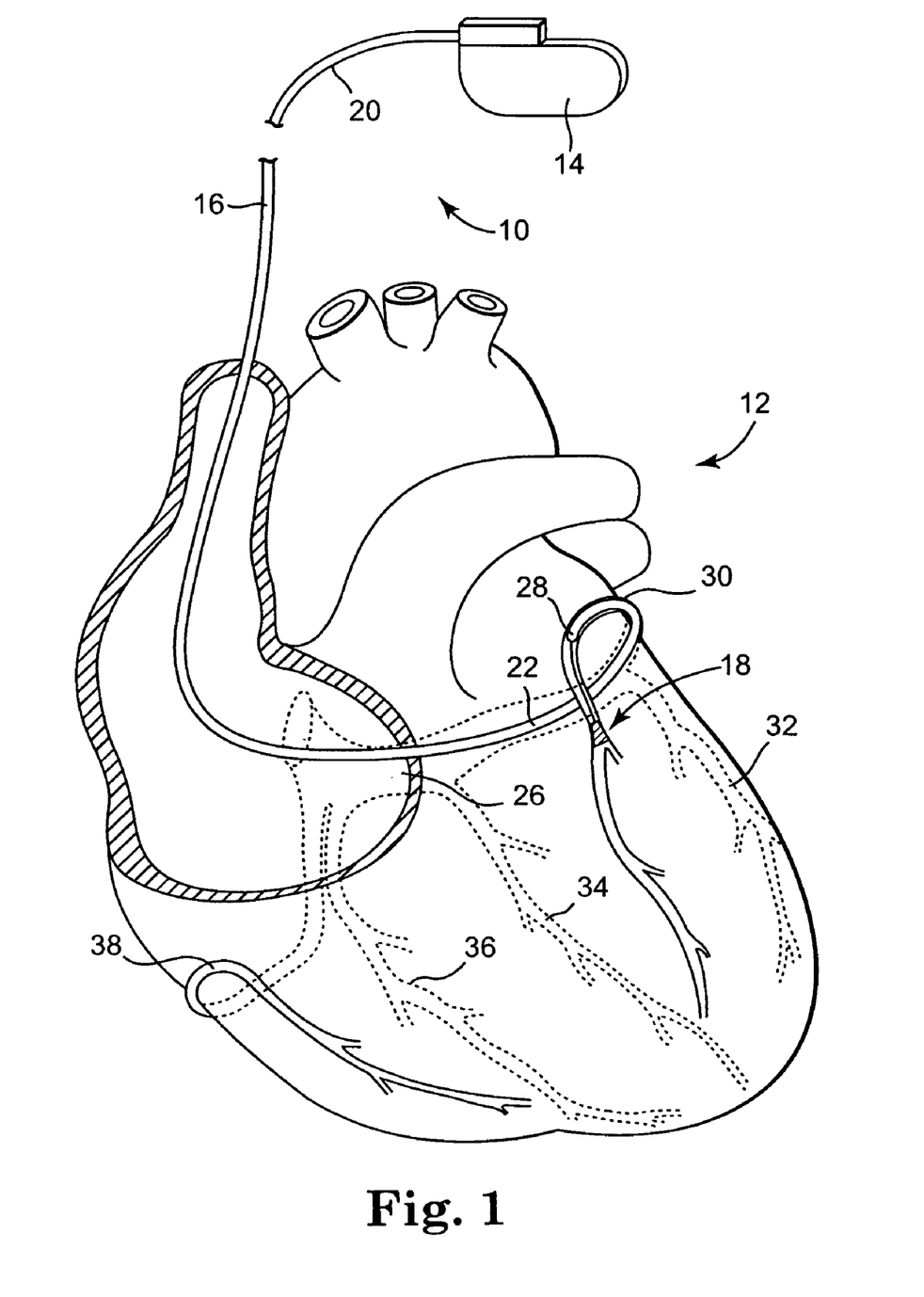
FIG. 1 is a partial sectional view of a cardiac rhythm management system implanted in a heart according to one embodiment of the present invention relative to a portion of the vasculature.

FIG. 1 shows a cardiac rhythm management ("CRM") system 10 deployed in a human heart 12 according to one embodiment of the present invention. The CRM system 10 includes a pulse generator 14, a lead body 16 coupled to the pulse generator 14, and an electrode delivery system 18. The lead 16 extends from a proximal end 20 coupled to the pulse generator 14 to a distal end 22 implanted in a branch vein of the coronary sinus 26. The lead 16 delivers electrical signals from the pulse generator 14 to an electrode 28 located at the distal end 22 to accomplish pacing of the heart 12. Once positioned in, for example, a branch of the great cardiac vein 30, the lead 16 can be used to sense the electrical activity of the heart 12 or to apply a stimulating pulse to the heart 12. In other embodiments, the lead 16 is positioned in any other branch vein of the coronary sinus 26 as is known in the art of cardiac function management. For example, it may be positioned in the left marginal vein 32, the left posterior ventricular vein 34, the middle cardiac vein 36 or the small cardiac vein 38.

Figure 2B:
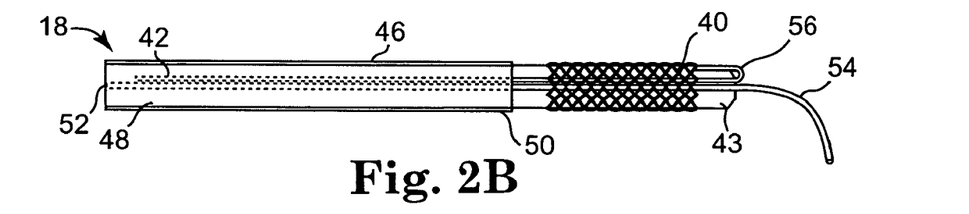
Figure 2C:
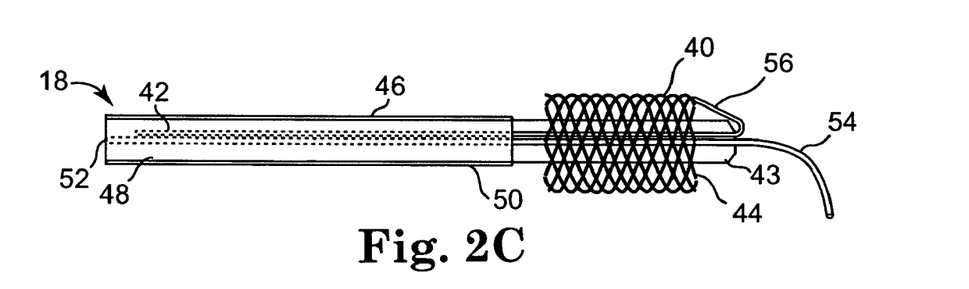

FIGS. 2A-2E show side views of the electrode delivery system 18 of FIG. 1 in various configurations during the lead anchor implantation process. As shown in FIGS. 2A-2C, the electrode delivery system 18 includes a stent-like mechanism 40 coupled to a flexible tether 42, a support structure such as a catheter 43, and a sheath 46. The stent-like mechanism 40 can have any of a variety of configurations in which the stent-like mechanism 40 is deployable from a first collapsed configuration to a second expanded configuration adapted to engage the inner walls of a vessel of the heart 12 with sufficient force to prevent dislocation. Although not limited to having a structure similar to a stent as is known in the art of cardiac stents, the stent-like mechanism 40 will hereinafter be referred to as "stent" 40 for convenience.

In the present embodiment, the stent 40 is an expandable, coiled member defining an internal lumen 44. The stent 40 is deployable from a first, collapsed configuration to a second, expanded configuration. The stent 40 also has a low profile in the collapsed configuration that is adapted to be inserted into vessels having small diameters. The stent 40 is disposed around an exterior of the catheter 43 and is encased in the sheath 46, which extends from a proximal end 48 to a distal end 50. As shown, the tether 42 extends proximally from the stent 40 through a lumen of the catheter 43.

The sheath 46 is removable from the stent 40 and is sized to retain the stent 40 in the first collapsed configuration when the stent 40 is encased therein, as is shown in FIG. 2A. While shown in FIGS. 2A-2C as a peel-away type sheath, sheath 46 may have other configurations and removal features as are known in the art. For example, the sheath 46 may be slidable over the catheter 43. Alternately, the sheath 46 is made from a dissolvable, biocompatible coating such as sugar disposed over the stent 40 but not necessarily extending over the length of the catheter 43. In this embodiment, the sheath 46 need not be manipulated or retracted, but instead dissolves to allow the stent 40 to deploy to the expanded configuration.

Figure 2D:
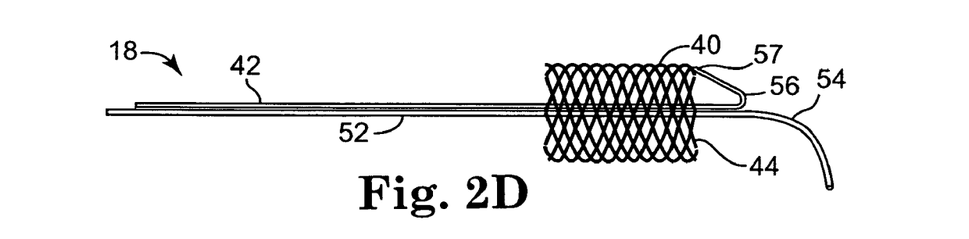
Figure 2E:
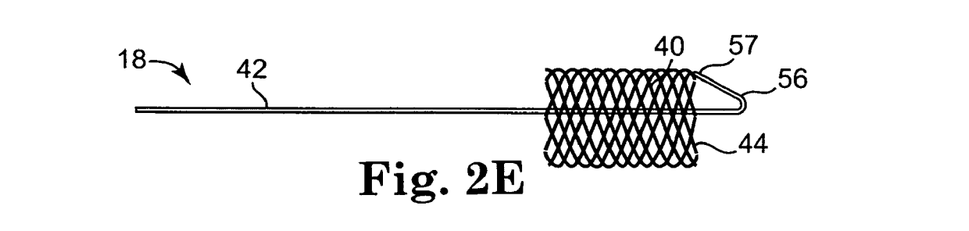

FIG. 2B shows the distal portion 50 of the sheath 46 partially retracted along the catheter 43, thereby exposing the stent 40. FIG. 2C shows the stent 40 deployed to an expanded configuration upon release from the distal end 50 of the sheath 46. The stent 40 may be self-expanding or may be, for example, balloon expanded. FIG. 2D shows the catheter 43 and the sheath 46 fully removed, such that the tether 42 and guide wire 52 are visible. FIG. 2E shows the guide wire 52 removed, leaving only the stent 40 and the tether 42. The system shown in FIG. 2E is configured to guide and secure an implanted cardiac lead 16.

The electrode delivery system 18 optionally includes a guide wire 52 to facilitate cannulating a vessel. The guide wire 52 extends through the catheter 43 so that a distal end 54 of the guide wire 52 extends distally from the sheath 46. The guide wire 52 has a preformed curvature at the distal end 54 shaped to facilitate cannulating lateral branch veins of the coronary sinus 26. Alternately, the stylet distal end 54 is straight and deformable into a curved configuration at the time of implantation by the user. Other guide or delivery means suitable for cannulating the coronary sinus 26 and branch veins and guiding the stent 40 into the coronary sinus 26 may be substituted for the guide wire 52, including a stylet. Furthermore, the guide catheter 43 may be seated in the heart 12 without the guide wire 52.

Figure 3:
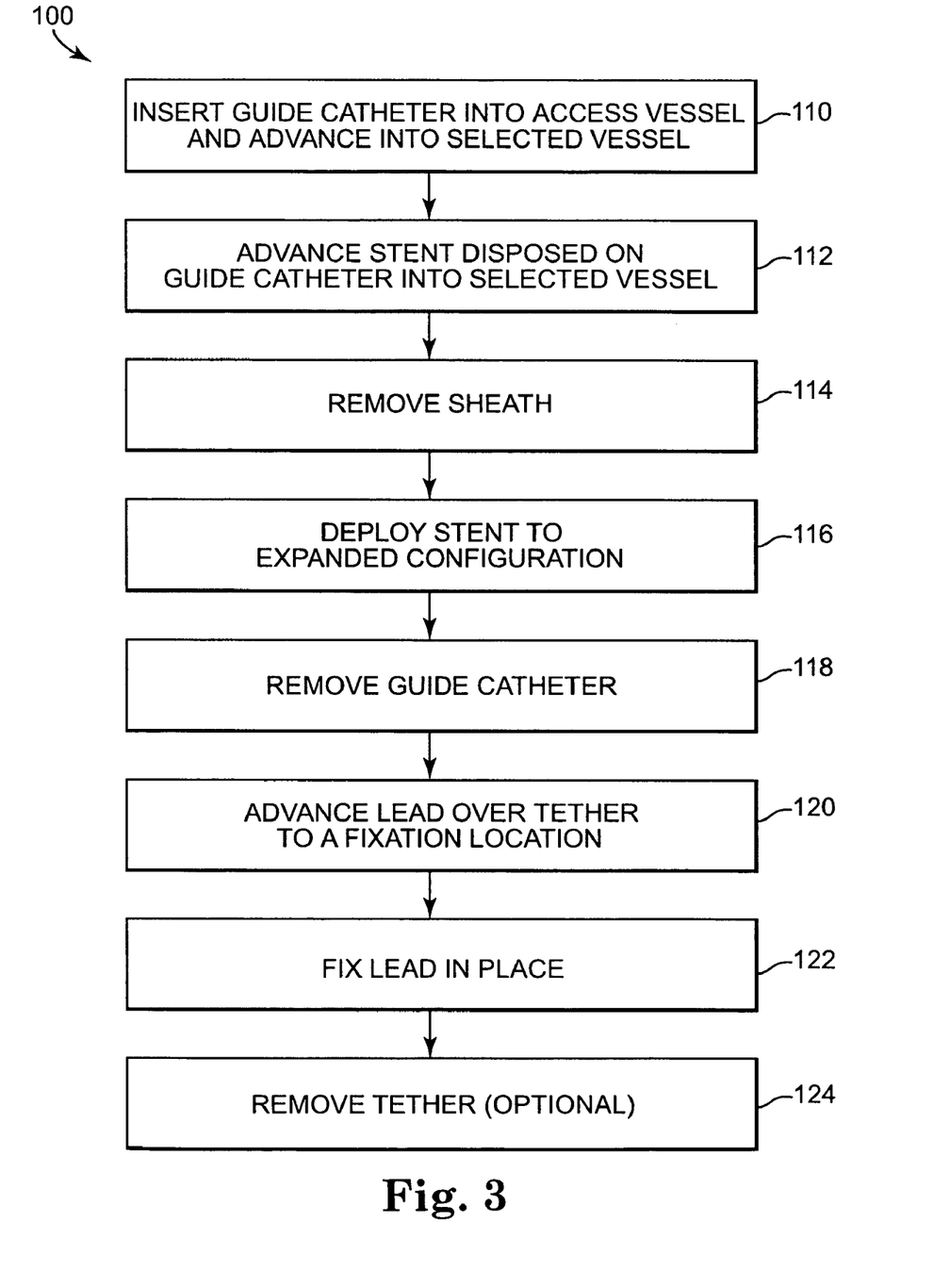
FIG. 3 is a flowchart detailing a method of implanting an electrode according to one embodiment of the present invention.

The electrode delivery system 18 is operable to seat the distal end 22 of the lead 16 in a selected vessel (as shown in FIG. 1) according to a method as illustrated in FIG. 3. The clinician manipulates the guide wire 52 through an access vessel and cannulates a selected vessel to slightly past an implant site (block 110). The shape of the distal end 54 of the guide wire 52 may be chosen or altered to facilitate access to a given vessel. The catheter 43 with the stent 40 disposed thereon is threaded onto the guide wire 52 and advanced towards the implant site near the distal end 54 of the guide wire 52 (block 112). In one embodiment, the tether 42 is semi-rigid and provides support as the catheter 43 and stent 40 are advanced over the guide wire 52. In another embodiment, a stylet (not shown) is used to stiffen the catheter 43 and facilitate cannulation through the vasculature. Alternately, the guide wire 52 and catheter 43 are assembled prior to insertion. The catheter 43 and stent 40 advanced along with the guide wire 52 as the vessel is cannulated.

Once positioned at the implant site, the sheath 46 is retracted from the stent 40 (block 114). Upon removal of the sheath 46 from around the stent 40, as is shown in FIGS. 2B and 2C, the stent 40 deploys to a second, expanded configuration (block 116). The stent 40 is sized such that upon deployment to the expanded configuration, the stent 40 frictionally engages the inner walls of the surrounding vessel with sufficient force to retain the stent 40 in place. This frictional engagement is sufficient to resist a proximally directed force exerted on the tether 42 as the catheter 43, sheath 46 and guide wire 52 are withdrawn proximally and removed (block 118). Following removal of the catheter 43 and guide wire 52, as shown in FIGS. 2D and 2E, the lead 16 is threaded onto the tether 42 and advanced over the tether 42 into the heart 12 (block 120).

The lead 16 may be advanced to any position along the tether 42. As shown in FIG. 2E, a portion of the distal end 56 of the tether 42 extends distally to the stent 40 and the remainder of the tether 42 extends proximally from the stent 40. Accordingly, the lead 16 may be advanced over the tether 42 to a fixation location distal to the stent 40. The distal end 56 of the tether 42 is sufficiently rigid to retain its shape even when tension is exerted thereon as the lead 16 is advanced over the tether 42. Once positioned in a desired location, the lead 16 is fixed in place. (block 122). The lead 16 can be fixed to the tether 42, or may include active fixation features as are known in the art for affixing to heart 12. Eventually, encapsulation tissue forms around the lead 16, providing further fixation to the heart 12.

In one embodiment, the tether 42 is detachable from the stent 40 (block 124). This is accomplished by, for example, dissolving a portion of the tether 42 or by rotating the tether 42 a pre-determined amount relative to the stent 40. In another embodiment, the tether 42 is provided with a weakened area 57 (see FIGS. 2D and 2E) adjacent the stent 40 to facilitate detachment. The tether 42 can thus be removed at implantation or at a later date if the lead 16 is extracted.

In another embodiment, the lead 16 is pre-loaded over the tether 42 prior to implantation. The catheter 43, stent 40, and lead 16 are advanced into the heart 12 together. Following deployment of the stent 40, the lead 16 can be withdrawn proximally over the tether 42, if desired, to a selected location.

Figure 4:
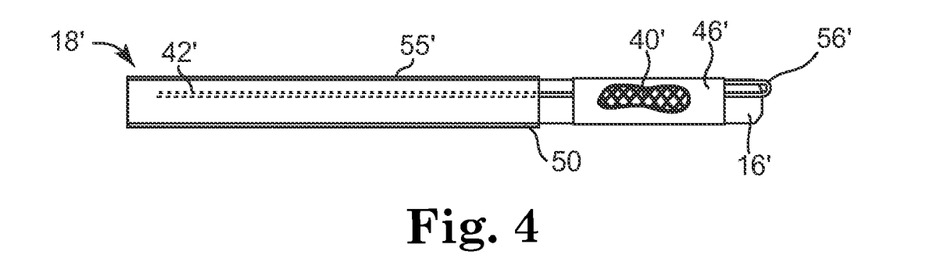
FIG. 4 is a side view of an electrode delivery system according to another embodiment of the present invention.

FIG. 4 shows an electrode delivery system 18' according to another embodiment of the present invention. Electrode delivery system 18' is generally similar to the electrode delivery system 18 of the previous figures and like parts are given like numbering. In the present embodiment, the lead 16' replaces the catheter 43 as the support structure for delivering the stent 40' into the heart 12. As is shown in FIG. 4, the stent 40' is disposed about the distal end of the lead 16'. The tether 42' is threaded through a lumen in the lead 16' as previously shown. The sheath 46', in this embodiment a dissolvable coating as previously described, is formed over the stent 40' and retains the stent 40' in the collapsed configuration about the lead 16'. To implant the lead 16' and stent 40', a guide catheter 55' is manipulated to cannulate a vessel of the heart 12. A stylet or guide wire may be employed as previously described to facilitate cannulation (not shown). After the guide catheter 55' is seated in the heart 12, the lead 16' is advanced through the guide catheter into the heart 12 so that the stent 40' is advanced beyond the guide catheter 55'. The stent 40' deploys to the expanded configuration upon dissolution of the sheath 46' and is fixed in place. The guide catheter 55' is removed and the lead 16' can be withdrawn proximally to a desirable implant location.

The stent 40 is optionally coated with a pharmacological, therapeutic or other agent or is formed from a drug-eluting material as is known in the art. According to one embodiment, the stent 40 is coated with a steroid. According to some embodiments, either or both of the tether 42 and stent 40 are formed from a material that is bioabsorbable or biodegradable. Such a bioabsorbable or biodegradable material may be chosen to dissolve after a period of time sufficient for encapsulation tissue to form around the lead 16 and fix the lead 16 in place near the implant site. According to one embodiment, the stent 40 is provided with a coating for preventing tissue ingrowth. Reduced tissue ingrowth would facilitate re-positioning or removal after an extended period of implantation. Such a coating might be a polymer, such as silicone or polyurethane. Alternately, the stent 40 is coated with expanded polytetrafluoroethylene (ePTFE), a microporous material used in GORETEX® fabrics. The porous structure of ePTFE is sized to permit fluid passage, while blocking tissue ingrowth.

Figure 5:
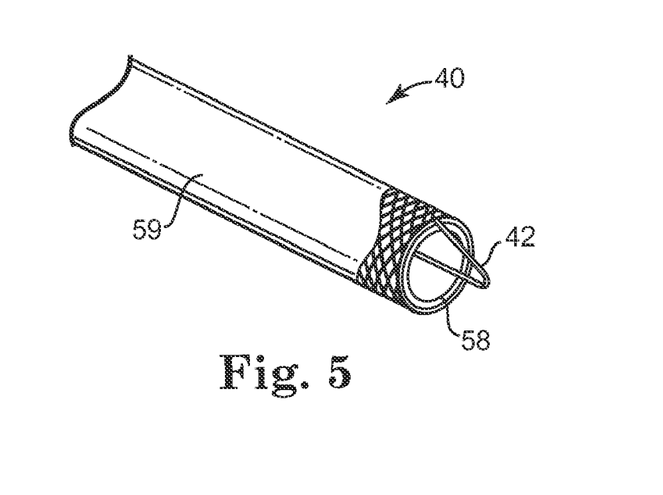
FIG. 5 is a partially cut-away view of an electrode delivery system according to another embodiment of the present invention.

In another embodiment, at least a first polymer member covers at least a portion of the stent 40. Preferably, as is shown in FIG. 5, the stent 40 is sandwiched between thin polymer sheets 58 and 59. The polymer members 58, 59 allow the stent 40 to expand and deploy, but prevent tissue ingrowth into any open spaces in the deployed stent 40.

In one embodiment, the lead 16 is biased to have a curvature at the distal end 22. The curvature can be chosen to facilitate implantation, to engage the inner walls of the vessel to anchor the lead 16 in place or to orient the electrode 28 within the vessel. Such a lead curvature is straightened out or neutralized by exerting tension on the tether 42 as the lead 16 is advanced through the vasculature. The tensioned tether 42 is then sufficiently rigid to overcome the biasing force of the lead curvature. The bias is re-instated at any time by relaxing the tensioning force on the tether 42. Where such lead curvature bias is sufficient to retain the lead 16 in a chosen position within the vasculature, the lead 16 is re-positioned simply by tensioning the tether 42, re-positioning the lead 16, and relaxing the tether 42.

According to still another embodiment of the present invention, the stent 40 itself serves as an electrode for facilitating sensing or pacing of the heart 12. A stent 40 having electrode capabilities may be used in combination with the lead 16 to provide bipolar pacing. Alternately, the stent 40 may be deployed without the lead 16 to provide pacing and sensing of the heart 12. In this embodiment, to facilitate electrode-like capabilities, the stent 40 and tether 42 are formed of conductive materials that may be electrically coupled to the pulse generator 14. The conductive material of the stent 40 is exposed to the tissue of the heart 12 to accomplish pacing and/or sensing while the conductive material of the tether 42 is shielded from exposure to tissues as it extends from the electrode/stent 40 to the pulse generator 14.

Figure 6A:
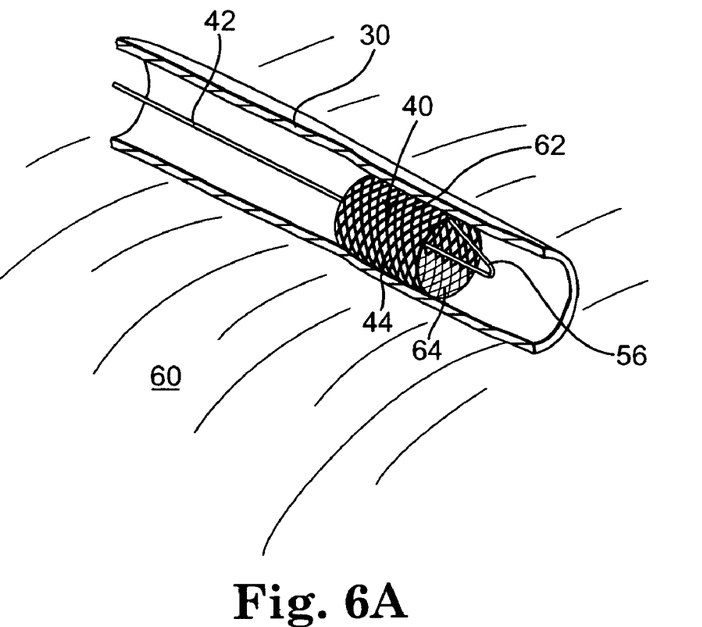
FIG. 6A is a partially cut-away view of an electrode delivery system according to one embodiment of the present invention deployed in a vein.

FIG. 6A shows the stent 40 deployed in the great cardiac vein 30 extending over the epicardial surface 60 of the heart 12. A substantial portion of the stent 40 is covered or coated with an insulating material 62 which extends over approximately 270 degrees circumferentially about the stent 40, while approximately 90° remains exposed, forming an electrically active region 64 extending axially for the length of the stent 40. In another embodiment, the insulating material 62 extends from about 150 to about 300 degrees circumferentially about the stent 40.

Figure 6B:
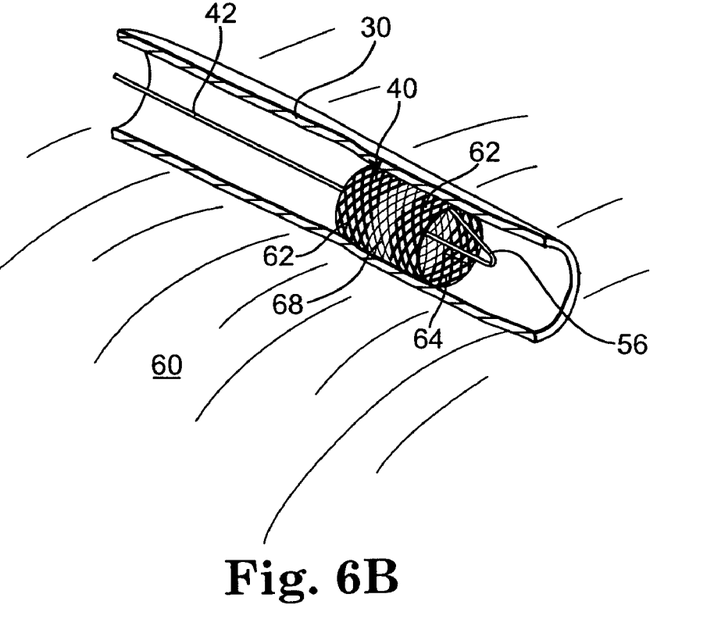
FIG. 6B is a partially cut-away view of an electrode delivery system according to another embodiment of the present invention deployed in a vein.

It is important that the exposed region 64 of the stent 40 be positioned to make reliable contact with the heart 12. For example, it is more desirable for the exposed region 64 to contact the epicardial surface 60 of the heart 12, as is shown in FIG. 6B, than an outer facing surface of the implant vessel. The exposed region 64 of the stent 40 may be flattened or shaped with a slightly concave or convex profile corresponding to the surface of the heart 12 to facilitate positioning the exposed region 64 on the surface 60 of the heart 12. Alternately, the stent 40 is rotatable or otherwise maneuverable by the surgeon to position the exposed region 64 on a particular surface of the heart 12.

Despite the configuration of the stent 40 and maneuverability features, it may still be difficult to accurately position the exposed region 64 over a chosen surface. Therefore, in other embodiments, the exposed region 64 completely encircles a region of the stent 40 as is shown in FIG. 6B. These configurations are not intended to be limiting, rather a variety of configurations are contemplated, including a stent 40 whose entire surface is exposed.

Figure 7:
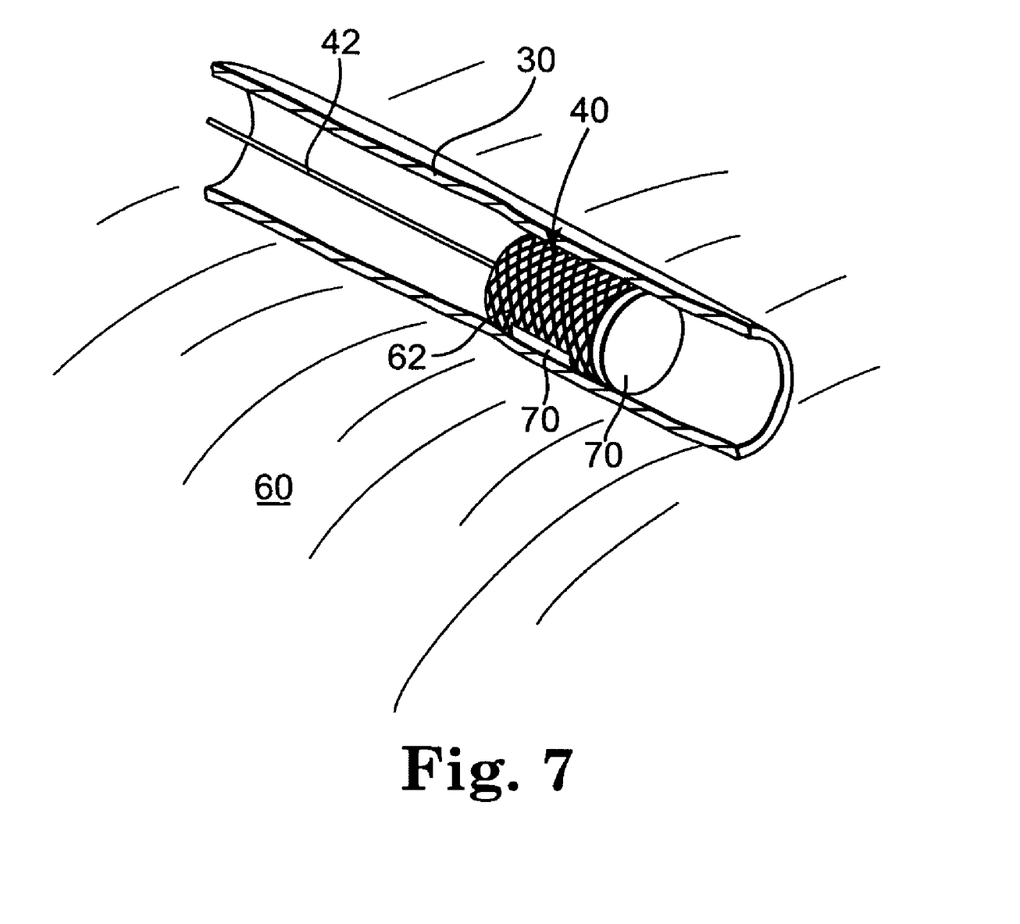
FIG. 7 is a partially cut-away view of an electrode delivery system including electrode according to another embodiment of the present invention deployed in a vein.

FIG. 7 shows another embodiment in which a separate electrode 70 is carried on the stent 40 and is electrically coupled to the tether 42, while remaining electrically isolated from the stent 40. The electrode 70 is sized to be retained in the sheath throughout delivery. FIG. 7 shows the electrode 70 shaped like a disc and carried near a distal end of the stent 40. However, the electrode 70 may have other configurations and be placed at other positions on the stent 40 to make good contact to the heart 12. The tether 42 is coupled directly to the electrode 70 and may be used to form an electrical connection between the electrode 70 and the pulse generator 14, similar to the embodiment described above. Alternately, a separate conductive member electrically couples the electrode 70 to the pulse generator 14 (not shown). The stent 40, in this embodiment, may be formed of a bioabsorbable material so that the stent 40 is absorbed after passage of sufficient time to allow sufficient tissue ingrowth to anchor the electrode.

According to one embodiment, the electrode delivery system 18 may be used to take preliminary electrical readings (e.g., pacing threshold) to "map" the adjacent tissue. Such readings are used to determine whether the tissue is appropriate for electrical stimulation. The stent 40 is partially deployed, i.e., only a portion of the sheath 46 is removed, as in FIG. 2B, allowing a small region of the stent 40 or the electrode 70 to deploy and make contact with the heart 12. After such partial deployment, electrical readings are taken. If the site is appropriate for electrode placement, the remainder of the sheath 46 is removed and the stent 40 is fully deployed. If the site is not appropriate for electrode placement, the partial deployment is reversed. This is accomplished by, for example, withdrawing the stent 40 into the sheath 46 or replacing the portion of the sheath 46 that was removed. The stent 40 is repositioned to locate a more appropriate site for sensing and/or pacing. Depending upon the degree of deployment, it may not be necessary to reverse the deployment to reposition the stent 40. Instead, the stent 40 may simply be advanced, withdrawn or rotated while in this partially deployed configuration. In one embodiment, electrical readings are used to optimize the radial disposition of the exposed region 64, as shown in FIG. 6A, of the stent 40.

Figure 8A:
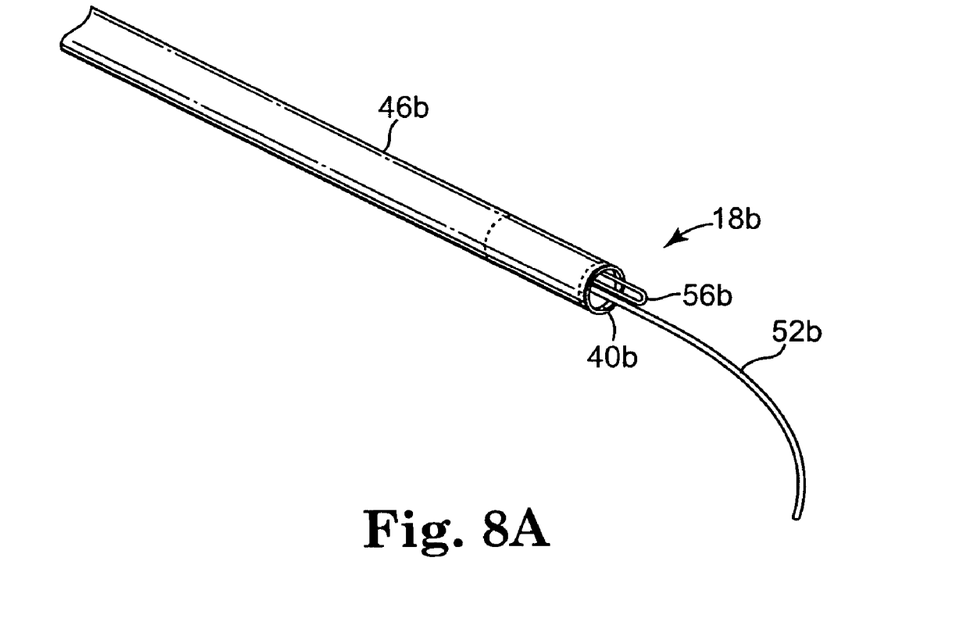
FIG. 8A is a side perspective view of an electrode delivery system in which the stent is self-expanding according to another embodiment of the present invention.
Figure 8B:
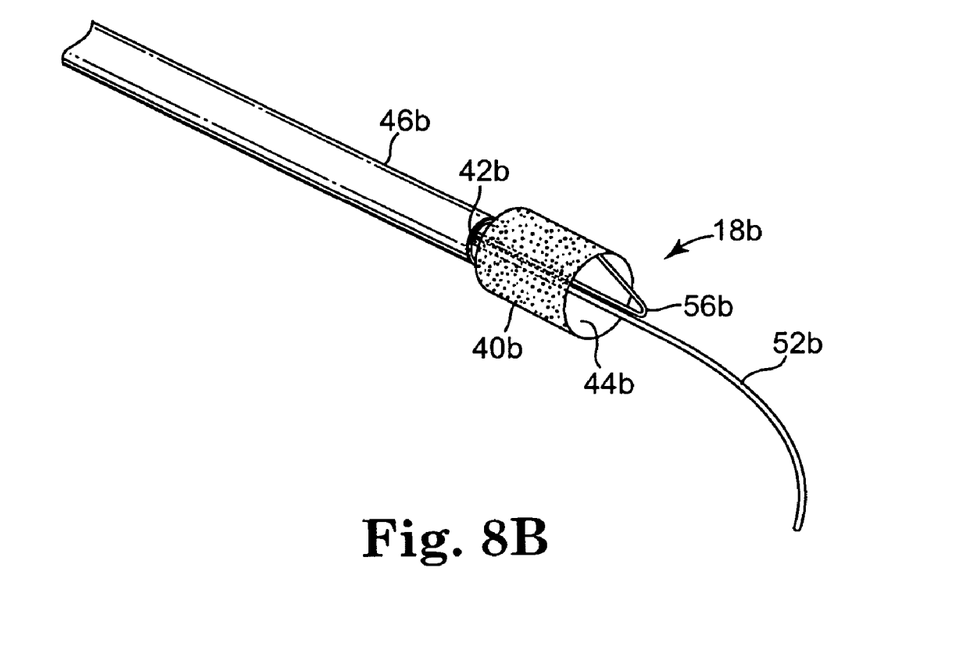
FIG. 8B is a side perspective view of the electrode delivery system of FIG. 8A in which the sheath is removed.

The stent 40 may have virtually any configuration as is known in the art of cardiac stents. The following figures show a few exemplary configurations of stent means for anchoring or delivering an electrode into a vessel, in addition to the stent means shown in FIGS. 1-7. FIGS. 8A and 8B show an electrode delivery system 18b according to another embodiment of the present invention, which is similar to the embodiments generally shown in FIGS. 2A-2E. Like parts are given like numbering. As shown in FIG. 8A, rather than having a coiled configuration, the stent 40b is formed of a material that is self-expanding. Upon removal of the sheath 46b and catheter (not shown), as is shown in FIG. 8B, the stent 40b deploys to an expanded configuration. The stent 40b may be formed of ePTFE, which as described previously, permits fluid passage but blocks tissue ingrowth. It is not necessary for the stent 40b to include the lumen 44 to permit fluid flow.

Figure 9A:
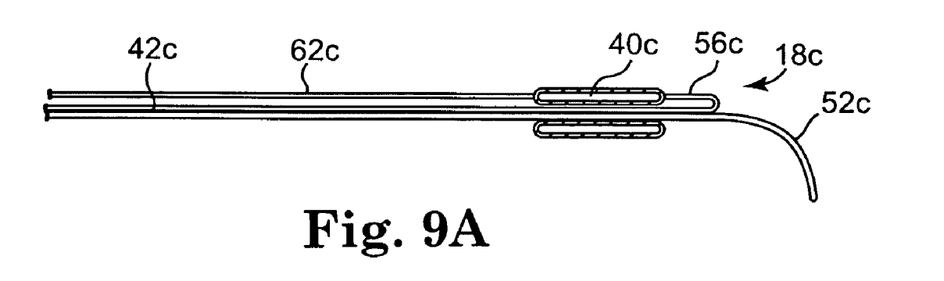
FIG. 9A is a sectional view of an electrode delivery system in which the stent is inflatable according to another embodiment of the present invention.
Figure 9B:
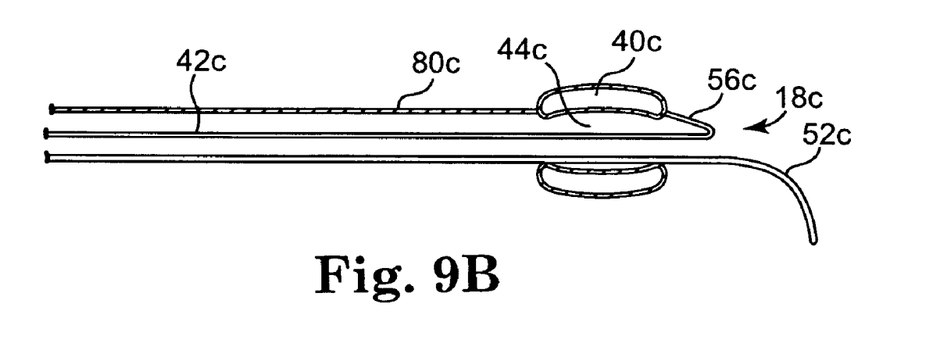
FIG. 9B is a sectional view of the electrode delivery system of FIG. 9A in which the sheath is removed and the stent is deployed.

FIGS. 9A and 9B show an electrode delivery system 18c according to another embodiment of the present invention, which is similar to the embodiments generally shown in FIGS. 2A-2E. As shown in FIGS. 9A and 9B, rather than being self-expanding, the stent 40c is an inflatable member. The stent 40c has an annular configuration defining the internal lumen 44c. The stent 40c is in fluid communication with a tubular member 80c for delivering deployment fluid. The inflated or deployed stent 40c, as shown in FIG. 9B, frictionally engages the walls of the surrounding vessel. While not shown, a catheter and sheath arrangement for facilitating delivery and implantation of the stent 40c, as is described and shown in relation to the embodiment generally shown in FIGS. 2A-2E, may also be employed.

Figure 10A:
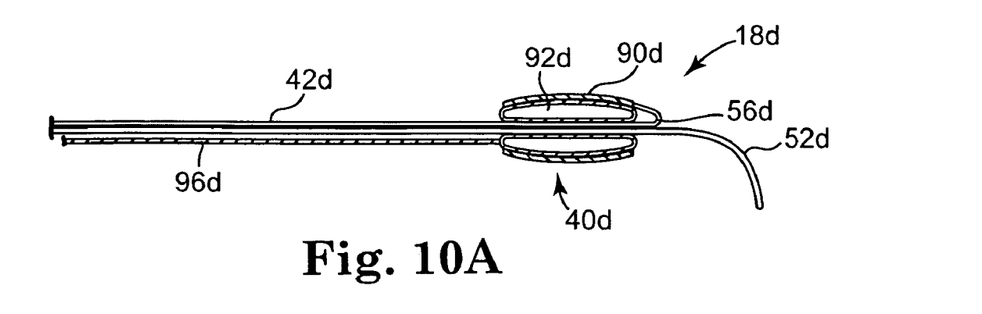
FIG. 10A is a sectional view of an electrode delivery system according to another embodiment of the present invention.
Figure 10B:
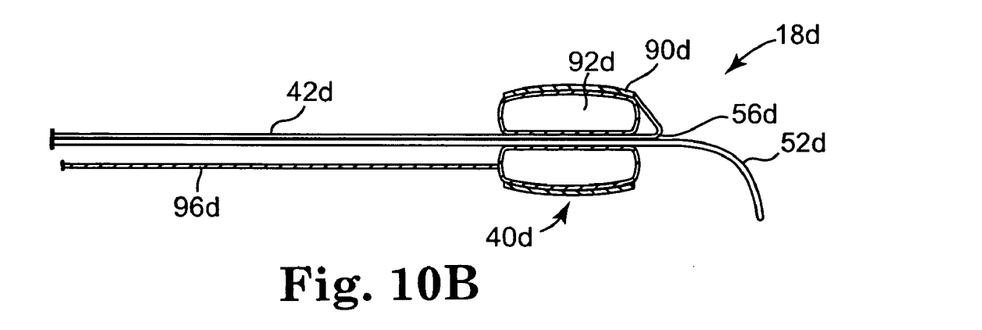
FIG. 10B is a sectional view of the electrode delivery system of FIG. 10A in which the inflatable member is inflated.
Figure 10C:
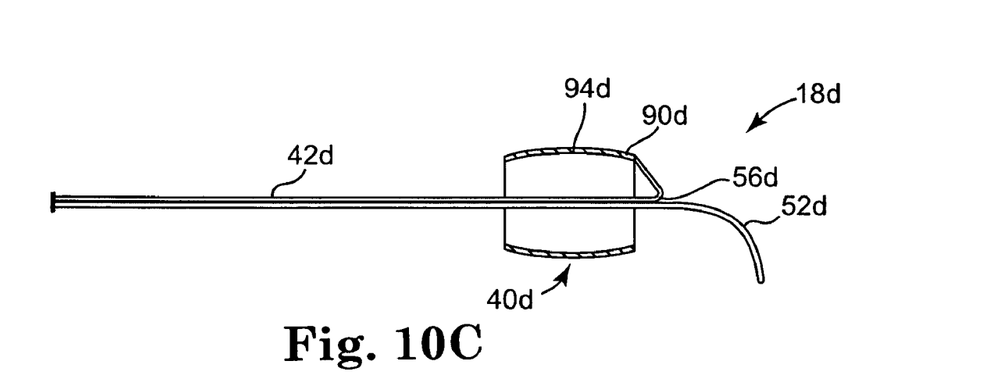
FIG. 10C is a sectional view of the electrode delivery system of FIG. 10B in which the inflatable member is removed.

FIGS. 10A-10C show an electrode delivery system 18d according to another embodiment of the present invention, which is similar to the embodiments shown generally in FIGS. 9A-9B. As shown in FIG. 10A, however, the stent 40d is formed of an expandable cage 90d disposed about an inflatable member 92d. The cage 90d is constructed of interlocking members 94d, visible in FIG. 10C, constructed such that upon deployment from a collapsed configuration to an expanded configuration, the cage members 94d lock in position, preventing subsequent collapse of the cage 90d. The inflatable member 92d is in fluid communication with a tubular member 96d for delivering deployment fluid. The stent 40d is advanced to a fixation location as previously described. When so positioned, the inflatable member 92d is inflated with the deployment fluid. This inflation expands the cage 90d from a collapsed configuration as shown in FIG. 10A to an expanded configuration as shown in FIG. 10B. The inflatable member 92d is deflated and optionally removed from within the cage 90d as shown in FIG. 10C. In one embodiment, the inflatable member 92d is a balloon. Again, while not shown, a catheter and sheath arrangement for facilitating delivery and implantation of the stent 40d, as is described and shown in relation to the embodiment generally shown in FIGS. 2A-2E, may also be employed.

Figure 11:
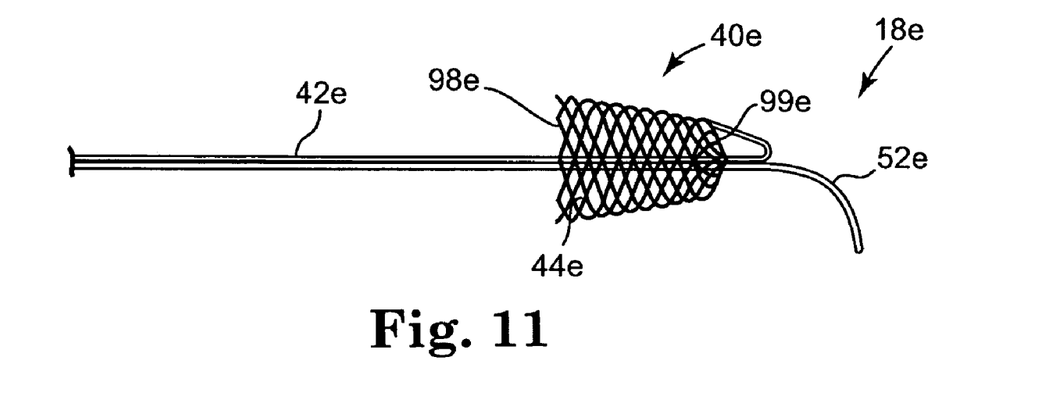
FIG. 11 is a side view of an electrode delivery system in which the stent has a tapered configuration according to another embodiment of the present invention.

FIG. 11 shows an electrode delivery system 18e according to another embodiment of the present invention, which is similar to the embodiments generally shown in FIGS. 2A-2E. As shown in FIG. 11, a stent 40e has a tapered configuration. The stent 40e has a greater diameter at a proximal end 98e and tapers to a smaller diameter at a distal end 99e. The stent 40e is inserted into a selected vessel as previously described and wedged into the vessel with sufficient force to frictionally engage the inner walls of the vessel and fix the stent 40e in place. The frictional force may be used to fix the stent 40e in a chosen position in place of the expandable configurations shown in the preceding embodiments, or in addition to an expandable feature to provide additional fixation support. Following insertion into the vessel, the lead 16 is advanced distally over a tether 42e coupled to the stent 40e and is wedged in a lumen 44e of the stent 40e at the proximal end 74e (not shown). Doing so improves lead fixation and reduces movement of the lead 16 with respect to the stent 40e.

Although the present invention has been described with reference to preferred embodiments, persons skilled in the art will recognize that changes may be made in form and detail without departing from the spirit and scope of the invention.

We claim:

1. An electrode delivery system configured to deliver an electrode into a coronary vein, the electrode delivery system comprising:
a support structure having a proximal end and a distal end;
a stent deployable from a first collapsed configuration to a second expanded configuration, the stent disposed about the distal end of the support structure, the support structure being adapted to be removed from the stent to deploy the stent within the coronary vein, the stent sized to receive at least a portion of a lead carrying the electrode;
a tether attached to the stent, the tether having a first portion extending distal to the stent, the first portion having a proximal region coupled to the stent and a distal region, the tether having a second portion coupled to the distal region of the first portion and extending proximally from the distal region through the stent such that the lead can be advanced along the tether into the stent while the tether remains attached to the stent such that an electrode on the lead can be positioned at a desired location relative to the coronary vein; and a removable sheath disposed around the stent and sized to retain the stent in the first collapsed configuration, wherein, in the second configuration, the stent frictionally engages the coronary vein to anchor the tether.

2. The electrode delivery system of claim 1 wherein the stent is coated with a material adapted to reduce tissue ingrowth.

3. The electrode delivery system of claim 1 wherein the stent is coated with a drug-eluting material.

4. The electrode delivery system of claim 1 wherein either of the stent and the tether are formed from a material that is biodegradable or bioabsorbable.

5. The electrode delivery system of claim 1 wherein the tether is detachably coupled to the stent.

6. The electrode delivery system of claim 1 wherein the sheath is a dissolvable coating formed about the stent.

7. The electrode delivery system of claim 1 wherein the support structure is a catheter.

8. The electrode delivery system of claim 7 further comprising a cardiac lead having an electrode and an internal lumen extending therethrough for receiving the tether.

9. The electrode delivery system of claim 1 wherein the support structure is a cardiac lead, the cardiac lead having an electrode and an internal lumen extending therethrough for receiving the tether.

10. The electrode delivery system of claim 1 further comprising an electrode coupled to the stent, wherein the electrode is electrically coupled to the tether.

11. The electrode delivery system of claim 10 wherein the electrode is an electrically active region of the stent.

12. The electrode delivery system of claim 10 wherein the electrode has a concave shape to facilitate contacting a surface of the heart.

13. The electrode delivery system of claim 10 wherein the electrode is electrically isolated from the stent.

14. The electrode delivery system of claim 1, wherein the first portion extends from the stent at an angle such that the lead can be advanced along the tether through and distal of the stent.

15. A device configured to deliver an electrode into a branch vein of the coronary sinus, the device comprising:

a support structure;

an expandable stent means disposed about the support structure, the support structure being adapted to permit removable of the support structure from the expandable stent means to leave the expandable stent means within the branch vein, the expandable stent means for anchoring an electrode in the branch vein;

a tether having a distal end and a proximal end, wherein a first portion of the tether extends distal to the stent, the first portion having a proximal region coupled to the stent means and a distal region, the tether having a second portion coupled to the distal region of the first portion and extending proximally from the distal region through the stent means such that a lead can be advanced along the tether into the stent means in order to position an electrode on the lead at a desired location relative to the branch vein while the tether remains fixedly attached to the expandable stent means;

a sheath removably disposed about the stent means; and an electrode coupled to the stent means.

16. The device of claim 15 wherein the electrode is an electrically active region of the stent means, and further wherein the electrode is electrically coupled to the tether.

17. The device of claim 16 wherein the stent means is coated with a non-conductive material except for the electrically active region.

18. The device of claim 15 wherein the electrode is electrically isolated from the stent means.

19. The electrode delivery system of claim 15, wherein the first portion extends from the expandable stent means at an angle such that the lead can be advanced along the tether through and distal of the expandable stent means.

20. An electrode delivery system configured to deliver an electrode into a coronary vein, the electrode delivery system comprising:

an implantable lead including an electrode disposed on the implantable lead;

a support structure having a proximal end and a distal end;

a stent deployable from a first collapsed configuration to a second expanded configuration, the stent disposed about the distal end of the support structure, the support structure configured to permit removal of the support structure to deploy the stent within the coronary vein, the stent sized to accommodate the implantable lead;

a tether attached to the stent, the tether including a portion that extends distally of the stent such that the lead can be advanced along the tether into the stent in order to position the electrode at a desired location relative to the coronary vein while the tether remains attached to the stent; and a removable sheath disposed around the stent and sized to retain the stent in the first collapsed configuration, wherein, in the second configuration, the stent frictionally engages the coronary vein to anchor the tether.

* * * * *